United States Patent [19]

Ginhoux et al.

[11] 3,973,431
[45] Aug. 10, 1976

[54] DEVICE FOR THE RAPID MEASURING OF THE DEGREE OF HUMIDITY OF SUBSTANCES

[75] Inventors: Louis Ginhoux, Villeurbanne; Jacques Flesselles, Fleury les Aubrais, both of France

[73] Assignees: CGEE Alsthom, Levallois-Perret; Service d'Exploitation Industrielle des Tabacs et des Allumettes, Paris, both of France

[22] Filed: June 18, 1975

[21] Appl. No.: 587,801

[30] Foreign Application Priority Data
June 20, 1974 France .............................. 74.21503

[52] U.S. Cl. ................................................ 73/76
[51] Int. Cl.² ........................................... G01N 25/56
[58] Field of Search ................. 73/76; 34/224, 232, 34/243

[56] References Cited
UNITED STATES PATENTS
2,080,168  5/1937  Dietert .................................... 73/76

FOREIGN PATENTS OR APPLICATIONS
248,856  5/1947  Switzerland ............................ 73/76

*Primary Examiner*—James J. Gill
*Assistant Examiner*—Anthony V. Ciarlante
*Attorney, Agent, or Firm*—Haseltine, Lake & Waters

[57] ABSTRACT

Improvement for a device for the rapid measuring of the degree of humidity of substances comprising a diffuser intended for passing hot air produced in a stove or an oven through these substances, the said substances being contained in a cup, whose bottom is permeable to air and in which the desiccating of the substances under the action of the passing of the hot air is effected. The diffuser used is characterized in that it is constituted by a nozzle comprising a first diaphragm arranged on the same side as the oven and a second diaphragm arranged on the same side as the cup.

1 Claim, 4 Drawing Figures

DEVICE FOR THE RAPID MEASURING OF THE DEGREE OF HUMIDITY OF SUBSTANCES

The invention relates to an improvement for a device for the rapid measuring of the degree of humidity of substances, such as tobacco, matches, textiles, using a dessication method.

That method consists in making a hot air current flow, in determined conditions, through a given mass of the substance considered and in measuring the loss of mass which ensues.

One of the most currently used dessication methods is that described in French patent No. 769,498 by M. Beaudesson. With that method for facilities for implementing and using, a determined quantity of substance, which is measured before and after dessication, is treated for a certain given time. For that purpose, the substance is placed in a tared cup on a suitably tared and graduated weighing machine.

Dessication is obtained by an air current blown in by a ventilator, heated in an oven on an electrical resistance and distributed by a diffuser on the substance to be treated in the cup whose bottom is permeable to air. A shutter of the air inlet of the ventilator enables the adjusting of the flow of the air current so as to obtain, after the given lapse of time, at the output of the oven, an ideal temperature of the air which is as close as possible to 100°, it being necessary to apply a correction factor as a function of the difference in the temperatures recorded.

Although this method has given rise, as a whole, to very good results, it has been realised that various improvements could, to great advantage, be made to the device for the implementing thereof.

Thus, after numerous trials, it was possible to observe that a better homogeneization of the diffusion of the hot air through the substance and, subsequently, an improved efficiency in the dessication, could be obtained with a certain type of diffuser.

The invention gas, as its aim, an improved diffuser for the rapid measuring of the degree of humidity of substances.

The invention has as its object an improvement for a device for the rapid measuring of the degree of humidity of the substances comprising a diffuser intended for passing hot air produced in an oven through these substances, the said substances being contained in a cup whose bottom is permeable to air and in which the dessication of the substances is effected under the effect of the passing of the hot air, characterized in that the diffuser consists of a nozzle comprising a first diaphragm arranged on the same side as the stove and a second diaphragm arranged on the same side as the cup.

According to one characteristic, the nozzle consists of a cylindrical body having a circular cross-section, the first diaphragm is constituted by a flat ring concentric with the nozzle and having, in its central portion, a circular hole, and the second diaphragm is constituted by a circular plate drilled at its periphery with the nozzle, with a series of holes arranged substantially at right-angles to the ring of the first diaphragm.

The characteristics and advantages of the invention will become apparent from the description of an embodiment given by way of illustration in the accompanying drawings.

Figure 1:
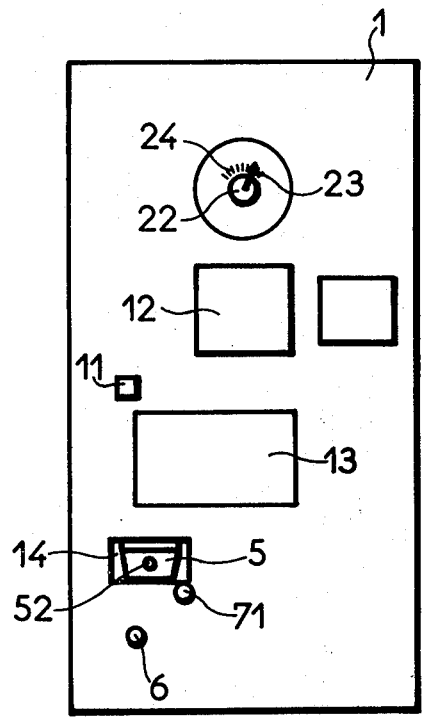
FIGS. 1 and 2 show a diagrammatic view of a device for the rapid measuring of the degree of humidity of substances.
Figure 2:
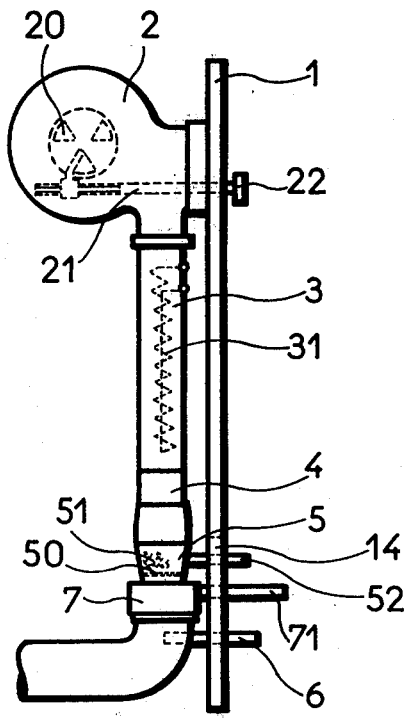
Figure 3:
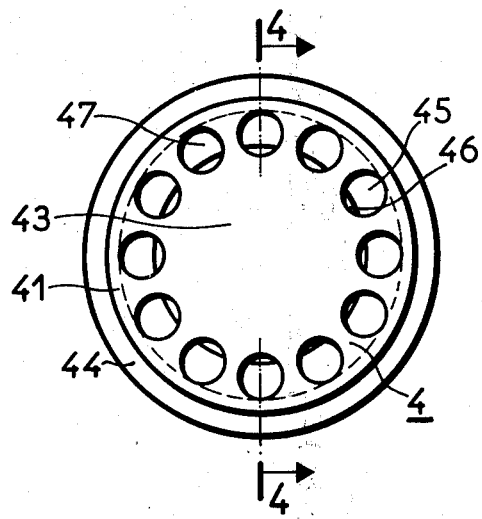
FIG. 3 shows a front view of the diffuser according to the invention.
Figure 4:
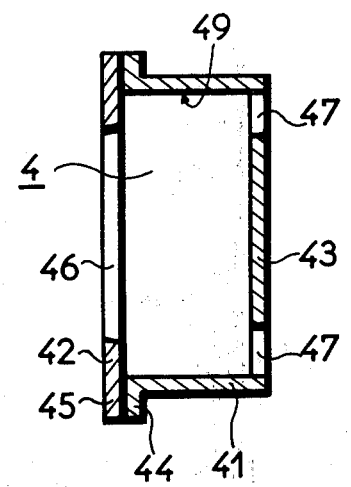
FIG. 4 shows a cross-section view of IV—IV' in FIG. 3.

In the figures, 1 designates a panel forming a frame and supporting a device for the rapid measuring of the degree of humidity of a substance. That device is essentially constituted by moto-ventilator unit 2, an oven 3, a diffuser 4, a cup 5 containing the substance to be treated and a control thermometer 6.

The ventilator comprises an air inlet provided with a shutter 20 enabling the adjusting of the air flow; that shutter can be operated by means of a threaded rod 21 and of a control knob 22 integral with a scale 23 moving opposite a graduation 24. The air sucked in by the ventilator is blown into the oven 3 where it is heated on an electric resistance 31; it emerges therefrom by means of the diffuser 4 which directs it into the cup 5. The substance 51 to be treated is arranged in that cup whose bottom is constituted by a metallic sieve 50 permeable to air. After the passing of the air through the substance 51, the thermometer 6 enables the measuring of the output temperature of the air. The clamping of the cup 5 against the diffuser 4 is provided for by a clamping collar fitted with an operating handle 71. The cup 5 is provided with a handle 52 enabling the operating thereof from the front face of the panel 11 through an opening 14.

According to the method, the following phases are carried out;

The cup is placed on a weighing machine and 10 grammes of the substance to be treated are spread out thereon. The cup and the substance are then arranged on the clamping device 7 and the cup is blocked against the diffuser 4 by means of the handle 71. The moto-ventilator unit 2 and the resistance 31 are fed with electric energy by means of a control unit 11 arranged on the panel 1. A time switch 12 placed on that panel cuts the supply after 5 minutes and the output temperature is read on the thermometer 6.

The cup is put back in place and the residue of tobacco is placed on the weighing machine and the loss of weight is observed on a graduation of the weighing machine directly divided into units of degree of humidity. If, despite the adjusting of the shutter 20, there is a difference in the output temperature of 100°, a correction factor indicated on a correction table 13 fixed on the panel is applied to that degree of humidity.

According to the invention, the diffuser 4 is constituted by a nozzle 41, a first diaphragm 42 arranged on the same side as the oven 3 and a second diaphragm 43 arranged towards the cup 5.

The nozzle comprises a cylindrical body 49 having a circular cross-section, one of whose ends comprises a circular shoulder 44 and whose other end comprises a bottom constituting the diaphragm 43. The first diaphragm 42 rests on the shoulder 44; it is constituted by a flat ring 45 resulting from the cutting out of its central portion into a circular hole 46. The second diaphragm 43 comprises, on its periphery, a series of holes 47 arranged substantially at right-angles to the full portion or ring 45 of the diaphragm 45.

The air inlet diaphragm 42 is arranged at the end of the oven 3, whereas the outlet diaphragm 43 is connected to the cup 5.

By means of this arrangement, it has been possible to observe a better distribution of the diffusion of the hot air through the mass of substance 51. Whatever its degree of humidity and its structure may be, it is practically certain that homogeneous dessication will always be obtained in the normal cycle of time of 5 minutes imposed by the time switch.

We claim:

1. Improvement in a device for the rapid measurement of the degree of humidity of substances comprising a diffuser intended for passing hot air produced in an oven through these substances, the said substances being contained in a cup whose bottom is permeable to air and in which the desiccation of the substances is effected under the effect of the passing of the hot air, the improvement consisting in a diffuser consisting of a cylindrical nozzle of circular cross section comprising a first diaphragm arranged on the same side as a stove having a flat ring concentric with said nozzle and having a circular hole in its central portion, a second diaphragm arranged on the same side as the cup constituted by a circular plate drilled at its periphery with the nozzle, with a series of holes arranged substantially at right-angles to the ring of the first diaphragm.

* * * * *